United States Patent [19]

Varma et al.

[11] Patent Number: 4,906,667
[45] Date of Patent: Mar. 6, 1990

[54] PHENYL HYDROXAMIC ACIDS INCLUDING A HETERO-CONTAINING SUBSTITUENT

[75] Inventors: Ravi K. Varma, Belle Mead; Eric M. Gordon, Pennington; Martin F. Haslanger, Ridgewood, all of N.J.

[73] Assignee: E. R. Squibb & Sons, Inc., Princeton, N.J.

[21] Appl. No.: 203,527

[22] Filed: May 23, 1988

Related U.S. Application Data

[63] Continuation of Ser. No. 891,812, Jul. 30, 1988, abandoned.

[51] Int. Cl.$^4$ .................... C07K 83/10; A61K 31/05; A61K 31/09; A61K 31/135
[52] U.S. Cl. .................... 514/575; 514/351; 514/352; 514/357; 514/507; 546/300; 546/309; 546/337; 560/315; 502/622
[58] Field of Search .................... 260/500.5 H, 545 R; 560/315; 546/300, 304, 337; 514/351, 352, 357, 507, 575, 576; 562/622

[56] References Cited

U.S. PATENT DOCUMENTS

| | | | |
|---|---|---|---|
| 3,479,396 | 11/1969 | Buu-Hoi et al. | 260/500.5 H |
| 3,560,519 | 2/1971 | Burk, Jr. et al. | 260/500.5 H |
| 3,681,445 | 8/1972 | Royle et al. | 260/500.5 H |
| 3,857,946 | 12/1974 | Shibata | 424/266 |
| 3,954,442 | 5/1976 | Becker et al. | 560/312 |
| 4,013,776 | 3/1977 | Lafon | 260/500.5 H |
| 4,029,815 | 6/1977 | Sherlock et al. | 260/500.5 H |
| 4,188,338 | 2/1980 | Bruins et al. | 260/500.5 H |
| 4,191,554 | 3/1980 | Gregory | 560/315 |
| 4,218,478 | 8/1980 | Omura et al. | 260/500.5 H |
| 4,604,407 | 8/1986 | Haslanger et al. | 260/500.5 H |
| 4,607,053 | 8/1986 | Karanewsky et al. | 260/500.5 H |
| 4,623,661 | 11/1986 | Summers | 260/500.5 H |

FOREIGN PATENT DOCUMENTS

0127726  12/1984  European Pat. Off.

OTHER PUBLICATIONS

Hawley, "the Condensed Chemical Dictionary", pp. 80 and 741, 8th ed., 1976.
"Websters Third New International Dictionary", unabridged, pp. 116 and 125, 1963.

Primary Examiner—J. E. Evans
Attorney, Agent, or Firm—Theodore R. Furman, Jr.

[57] ABSTRACT

Phenyl hydroxamic acids are disclosed having the general formula

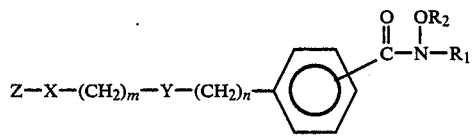

$$Z-X-(CH_2)_m-Y-(CH_2)_n-$$

or a pharmaceutically acceptable salt thereof, wherein X is NR, oxygen, sulfur,

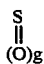

or a single bond, and Y is NR, oxygen, sulfur,

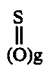

or a single bond, where R can be hydrogen or lower alkyl, g can be 1 or 2, and with the proviso that at least one of X and Y is other than a single bond; Z is aryl, aralkyl or cycloalkyl; $R_1$ is hydrogen, substituted or unsubstituted lower alkyl, cycloalkyl, lower alkenyl or aryl; $R_2$ is hydrogen, lower alkyl, aroyl or acyl; m is 0 to 4 carbon atoms; and, n is 0 to 4 carbon atoms further providing that if one of X or Y is oxygen, the other of X or Y must be oxygen and further that when X and Y are oxygen Z cannot be aralalkyl.

These new compounds have been found to be inhibitors or arachidonic acid 5-lipoxygenase and are therefore useful as antiallergy agents and antipsoriatics.

13 Claims, No Drawings

PHENYL HYDROXAMIC ACIDS INCLUDING A HETERO-CONTAINING SUBSTITUENT

This is a continuation of co-pending application Ser. No. 891,812 filed on Jul. 30, 1986 now abandoned.

FIELD OF THE INVENTION

The present invention relates to phenyl hydroxamic acid derivatives which include at least one hetero-containing substituent and more particularly concerns such derivatives which are inhibitors of arachidonic acid 5-lipoxygenase and as such are useful, for example, as antiallergy and antipsoriatic agents.

SUMMARY OF THE INVENTION

In accordance with the present invention new phenyl hydroxamic acid derivatives useful as $\Delta^5$-lipoxygenase inhibitors are provided. These new compounds have the general formula

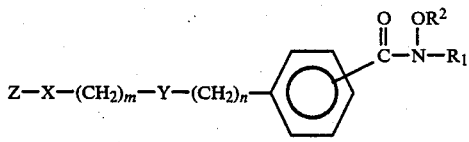

or a pharmaceutically acceptable salt thereof, wherein X is NR, oxygen, sulfur,

or a single bond, and Y is NR, oxygen, sulfur,

or a single bond, where R can be hydrogen substituted alkyl or lower alkyl, g can be 1 or 2, and with the proviso that at least one of X and Y is other than a single bond; Z is aryl substituted aryl, aralkyl or cycloalkyl; $R_1$ is hydrogen, lower alkyl substituted alkyl, cycloalkyl, lower alkenyl or aryl; $R_2$ is hydrogen, lower alkyl substituted alkyl, aroyl or acyl; m is 0 to 4; and, n is 0 to 4 carbon atoms further providing that if one of X or Y is oxygen, the other of X or Y must be oxygen and further that when X and Y are oxygen Z cannot be aralalkyl. Further in accordance with the present invention, a method for using the above compounds is provided.

DETAILED DESCRIPTION OF THE INVENTION

The hydroxamic acid derivatives of the present invention where $R_2$ is hydrogen may form salts with alkali metals, such as lithium, sodium or potassium. In addition, the compounds of formula I will form weak salts with dicyclohexylamine or other amines as well as with tris(hydroxymethyl)aminomethane, glucamine and other amines as set out in U.S. Pat. No. 4,294,759. The compounds of the invention wherein X or Y are NR and wherein Z is 2, 3 or 4-pyridyl will form salts with acids, e.g. hydrochloric acid and the like.

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl or dodecyl.

The term "substituted alkyl" as employed herein refers to an alkyl group as described above including a halo-substituent F, Br, Cl or I or $CF_3$, an alkoxy substituent, an alkyl-aryl substituent, a haloaryl substituent, a cycloalkyl substituent, an alkylcycloalkyl substituent, hydroxy, an alkylamino substituent, an alkanoylamino substituent, an arylcarbonylamino substituent, a nitro substituent, a cyano substituent, a thiol substituent or an alkylthio substituent.

The term "cycloalkyl" employed herein by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, which groups are substituted with the same, or a different cycloalkyl.

The term "aryl" or "Ar" as employed herein by itself or as part of another group refers to monocyclic or bicyclic aromatic groups containing from 6 to 10 carbons in the ring portion, such as phenyl, or naphthyl.

The term "substituted aryl" refers to substituted pyridyl, substituted phenyl or substituted naphthyl wherein the substitutent on either the phenyl, or naphthyl may be, 1 or 2 halogens selected from chlorine, bromine or fluorine, 1 or 2 lower alkoxy groups, 1 or 2 hydroxyl groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

The term "aralkyl", "aryl-alkyl" or "aryl-lower alkyl" as used herein refers to lower alkyl groups as discussed above having an aryl substituent, such as benzyl.

The term "lower alkenyl" or "alkenyl" as employed herein by itself or as part of another group includes an unsaturated hydrocarbon group having from 2 to 8 carbons and a single carbon-carbon double bond, such as ethenyl, 1-propenyl, 2-propenyl, 1-butenyl, 2-butenyl, 3-butenyl and the like.

The term "acyl" as used herein by itself or as part of another group refers to an alkyl carbonyl or alkenyl carbonyl group.

The term "aroyl" as used herein by itself or as part of another group refers to an aryl carbonyl group.

The term "halogen" or "halo" as used herein refers to chlorine, bromine, fluorine or iodine with chlorine being preferred.

Preferred are those compounds of the invention wherein X is O, Y is O or NH, Z is phenyl, $R_1$ is $CH_3$, $R_2$ is H, m=2, and n=0.

The various compounds of the invention may be prepared as described below.

To make compounds of formula I wherein X is NR, R is hydrogen, Y is a single bond and Z is phenyl, a carboxylic acid of the formula

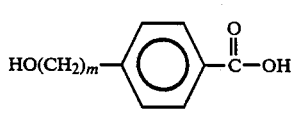

in an organic solvent, e.g. dichloromethane and methanol, is added to a solution of ethereal diazomethane to afford a compound of the formula

  III

A solution of the compound of formula III and p-toluenesulfonyl chloride in pyridine can be reacted at a temperature of within the range of from about 0° C. to about 25° C. to obtain a compound of the formula

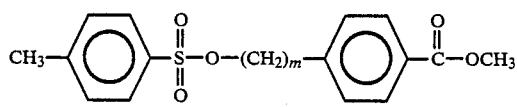  IV

Compound IV can be reacted with aniline and anhydrous sodium bicarbonate in the presence of hexamethylphosphoric triamide (HMPA) at a temperature between about 25° C. and 70° C. to provide a compound having the formula

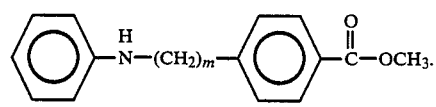  V

Compound V can thereafter be reacted with benzyl bromide, and anhydrous sodium bicarbonate in the presence of HMPA to afford a compound having the formula

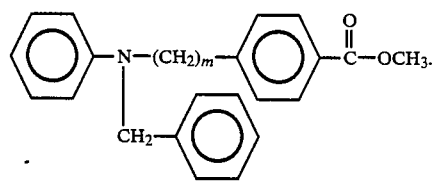  VI

A mixture of compound VI with lithium hydroxide in a solution of dioxane and water produces a carboxylic acid of the formula

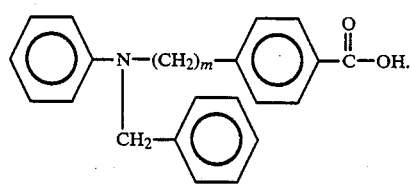  VII

A chlorinating agent, e.g. oxalyl chloride or thionyl chloride, is added to a mixture of compound VII in a solution of a solvent, e.g. benzene, and a catalytic amount of dimethylformamide at a temperature between about 0° C. and 25° C. to produce compound VIII having the formula

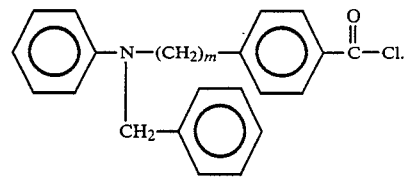  VIII

A solution of compound VIII in a solvent, e.g. tetrahydrofuran, can be reacted with a compound of the formula

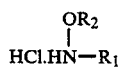  IX in the presence of an organic base, e.g. triethylamine, to obtain a compound of the formula

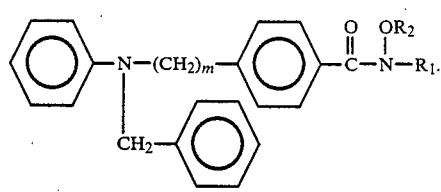  X

A mixture of compound X and 5% palladium on carbon in a solvent, e.g. methanol, can thereafter be hydrogenated at about room temperature and atmospheric pressure to afford the compounds of the invention having the formula

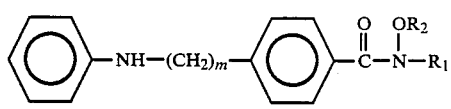  XI that is, compounds of formula I wherein X is NR, R is hydrogen, Y is a single bond, Z is phenyl and n=0.

To make compounds of the invention as in formula XI but where the phenyl is substituted with hydroxy, the compound of formula II can be reacted with N-bromosuccinimide in the presence of triphenyl phosphine and an organic solvent, e.g. benzene, at a temperature in the range between 0° C. and 25° C. This produces a compound of the formula

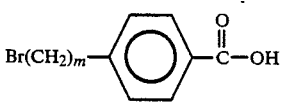  XII which when reacted with a chlorinating agent, e.g. oxalyl chloride, in the presence of an organic solvent, such as benzene, preferably in the presence of a small amount of dimethylformamide at a temperature in the range between 0° C. and 25° C. affords a compound of the formula

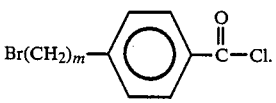  XIII

A compound of the formula

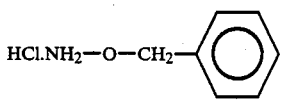
XIV can be reacted with a compound of the formula

XV   R₁—Br in the presence of dry HMPA and dry NaHCO₃ to obtain a compound of the formula

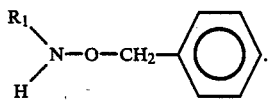
XVI

Compounds XVI and XIII, each in solution in an organic solvent, e.g. tetrahydrofuran, and in the presence of triethylamine can be reacted in a molar ratio of between about 1:1 and 2:1 and at a temperature within the range from about 0° C. to 25° C. to afford a compound of the formula

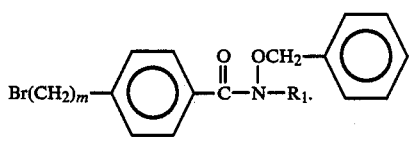
XVII

The compound of formula XVII is thereafter reacted with p-aminophenol in the presence of HMPA and dry NaHCO₃ under nitrogen at a temperature of between about 0° C. and 25° C. to produce a compound of the formula

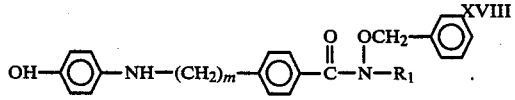
XVIII

Compound XVIII can then be reacted in an organic solvent, e.g. methanol, in the presence of 5% palladium on carbon under hydrogen atmosphere to yield compounds of the invention having the formula

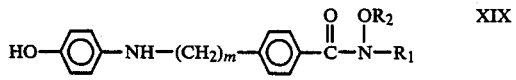
XIX that is, compound of formula I wherein X is NR, R is hydrogen, Y is a single bond, Z is phenyl substituted with hydroxy and n=0.

To obtain compounds of the present invention wherein Z is aralkyl and X and Y are oxygen, alpha-bromophenetole can be reacted with p-hydroxybenzoic acid in the presence of a base such as sodium hydride in an organic solvent such as dimethylformamide in a molar ratio from between about 1:1 to about 1:2, and at a temperature within the range from about 0° C. to 60° C. to form a mixture of the compound

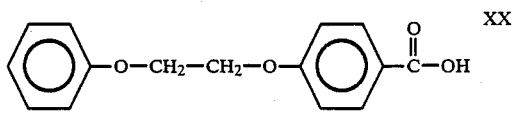
XX and the p-hydroxybenzoic acid. This mixture, when reacted in a solvent, e.g. methanol, and chloroform with diazomethane in ether yields an ester compound of the formula

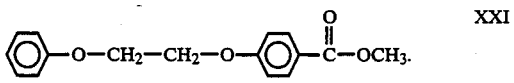
XXI

A solution of compound XXI in a solvent, e.g. tetrahydrofuran, can thereafter be subjected to an alkali metal hydroxide such as lithium hydroxide to afford a compound of the formula

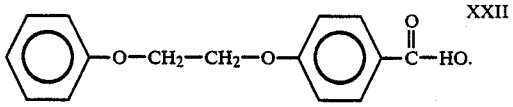
XXII

Compound XXII and a chlorinating agent, e.g. oxalyl chloride in a solvent, e.g. benzene, is treated with a catalytic amount of dimethylformamide under nitrogen at a temperature within the range of from about 0° C. to about 25° C. The acid chloride so-formed can then be dissolved in, for instance, tetrahydrofuran and subjected to a solution of methylhydroxylamine hydrochloride and triethylamine to afford a compound having the formula

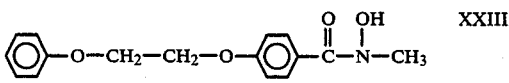
XXIII that is, a compound of formula I wherein X is oxygen, Y is oxygen and Z is aralkyl.

To obtain compounds of the invention wherein X is a single bond, Y is NR, R is hydrogen, n=0 and Z is phenyl, a benzoate of the formula

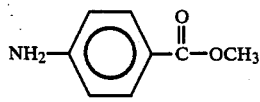
XXIV can be reacted with benzyl bromide in the presence of anhydrous sodium bicarbonate and a solvent, e.g. dry HMPA, under nitrogen at a temperature within the range of from about 0° C. to 70° C. to afford a compound of the formula

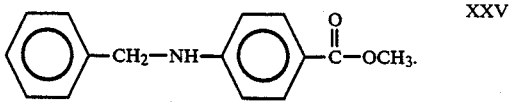
XXV

Compound XXV can be reacted with a halogenated phenylalkane of the formula

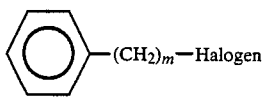 XXVI

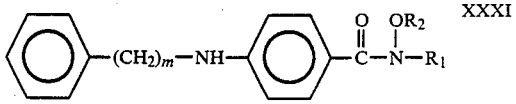 XXXI (e.g. 1-bromo-3-phenylpropane for the case where m is 3) in a molar ratio of from about 1:1 in the presence of a dry organic solvent, e.g. tetrahydrofuran and a base such as sodium hydride or n-butyllithium in hexane. This reaction, which can be carried out at a temperature within the range of from about 0° C. to about 25° C., affords a compound of the formula

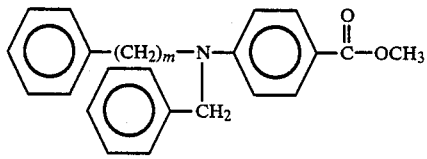 XXVII

By subjecting compound XXVII to an alkali metal hydroxide, such as lithium hydroxide in the presence of water and an organic solvent, e.g. dioxane or methanol, a product of the formula

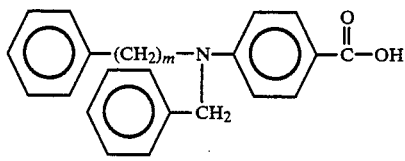 XXVIII is obtained.

The carboxylic acid XXVIII can thereafter be treated with oxalyl chloride in the presence of a catalytic amount of dimethylformamide and a solvent, e.g. benzene, to produce

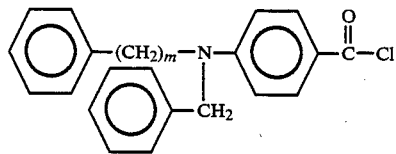 XXIX

Compound XXIX can be reacted with the compound of formula IX in the presence of triethylamine, an organic solvent, e.g. tetrahydrofuran and water at a temperature within the range between about 0° C. and 25° C. to afford compound

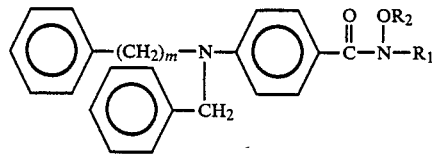 XXX

This compound can be subjected to 5% palladium on carbon in the presence of hydrogen and an organic solvent, such as methanol, to produce the compound of the invention that is, a compound of formula I wherein X is a single bond, Y is NR, R is hydrogen, Z is phenyl and n=0.

The compounds of the invention are $\Delta^5$-lipoxygenase inhibitors and prevent leukotriene $C_4$ formation in macrophages (Samuelsson, B., Science, Vol. 220, p. 568–575, 1983). The administration of compounds of this invention to humans or animals provides a method for treating allergy of a reagin or non-reagin nature. Asthma is preferably treated but any allergy wherein leukotrienes are thought to be involved as pharmacological mediators of anaphylaxis can be treated. For example, the compounds of this invention can be used for treatment of such conditions as allergic rhinitis, food allergy and urticaria as well as asthma and psoriasis.

An effective but essentially non-toxic quantity of the compound is employed in treatment.

The compounds of the invention can be administered orally, parenterally or topically to various mammalian species known to be subject to such maladies, e.g., humans, cattle, horses, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution, suspension cream, ointment or lotion containing about 5 to about 5000 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following examples represent preferred embodiments of the present invention.

EXAMPLE 1

N-Hydroxy-N-methyl-4-[3-(phenylamino)-propyl]benzamide

A. 4-(3-Hydroxy propyl)benzoic acid 1.7M n-butyllithium in hexane (19.4 ml, 33 mmole) was added dropwise to a chilled (−78° C.) and stirred solution of diisopropylamine (4.63 ml, 33 mmole) in 20 ml of dry tetrahydrofuran (hereinafter THF). After 20 minutes, a solution of p-toluic acid (2.042 g, 15 mmole) in 20 ml of dry THF was added dropwise. After stirring at −78° C. for another 1.5 hours, 4 ml of HMPA was added followed immediately by a solution of ethylene oxide (2.99 g, 67.9 mmole) in 10 ml of dry THF. The resulting solution was stirred at −78° C. for 2 hours, treated with 5% hydrochloric acid and warmed up to room temperature, the THF being removed in vacuo. The aqueous solution was saturated with sodium chloride and extracted three times with ethyl ether. The combined ether extracts were concentrated from 300 to 100 ml and extracted with a 0.5N sodium hydroxide solution. This extract was acidified with 10% hydrochloric acid and extracted three times with ethyl ether.

The ether extracts were dried over anhydrous magnesium sulfate and evaporated to a residue. This residue was chromatographed on a silica gel column, eluting successively with dichloromethane-ethyl acetate (9:1 and 1:1), ethyl acetate and dichloromethane-methanol (9:1) to give 750 mg of the title A compound, with consistent spectral data.

B. 4-(3-Hydroxy propyl)benzoic acid, methyl ester

To a solution of title A compound (750 mg, 4.16 mmole) in a mixture of 50 ml of dichloromethane and 10 ml of methanol was added a solution of ethereal diazomethane until a yellow color persisted. After stirring for 30 minutes, the excess diazomethane was destroyed by a few drops of glacial acetic acid. The solvent was evaporated in vacuo to give 800 mg of title B compound, with consistent spectral data.

C. 3-[(4-Methoxy carbonyl)phenyl]-propanol p-toluene sulfonic acid ester

A solution of title B compound (250 mg, 1.29 mmole) and p-toluenesulfonoyl chloride (493 mg, 2.59 mmole) in 7 ml of dry pyridine was stirred at room temperature under nitrogen for 4 hours. The resulting solution was poured into a cold 10% hydrochloric acid solution, saturated with sodium chloride and extracted three times with ethyl ether. The combined ether extracts were dried over anhydrous magnesium sulfate and evaporated to give 386 mg of title C compound, with consistent spectral data.

D. [N-[3(4-Methoxy carbonyl)phenyl]propyl]aniline

A mixture of title C compound (1.0 g, 2.87 mmole), aniline (267 mg, 2.87 mmole) and anhydrous sodium bicarbonate (360 mg, 4.3 mmole) in 7 ml of dry HMPA was stirred at 85° C. under nitrogen for 7 hours. The resulting solution was cooled to room temperature, diluted with 25 ml of water and extracted with ethyl ether. The ether extract was washed several times with water, dried over anhydrous magnesium sulfate and evaporated to produce an oil. The oil was chromatographed on a silica gel column to give 500 mg of title D compound, with consistent spectral data, as an oil.

E. [N-[N-[3-(4-Methoxy carbonyl)phenyl]propyl]benzyl] aniline

A mixture of title D compound (1.1 g, 4.08 mmole), benzyl bromide (768 mg, 4.49 mmole) and anhydrous sodium bicarbonate (515 mg, 6.13 mmole) in 15 ml of dry HMPA was stirred at 70° C. under N₂ for 3 hours. The resulting solution was cooled to room temperature, poured into 50 ml of cold water and extracted twice with ethyl ether. The combined extracts were washed, dried over magnesium sulfate and evaporated to give an oil which was chromatographed to yield 1.1 g of title E compound, with consistent spectral data, as a solid.

F. [N[N-[3-(4-Carboxy)phenyl]propyl]benzyl] aniline

A mixture of title E compound (1.1 g, 3.06 mmole) and lithium hydroxide (1.0 g) in a mixture of 20 ml of dioxane and 10 ml of water was refluxed under nitrogen for 2 hours. The resulting solution was cooled to room temperature, adjusted to a pH of 5.5 with 5% hydrochloric acid and most of the dioxane was removed in vacuo. The residual slurry was saturated with sodium chloride and extracted three times with ethyl acetate. The combined extracts were dried over anhydrous magnesium sulfate and evaporated to give 1.05 g of title F compound, with consistent spectral data, as a solid.

G. [N-[N-[3-(4-Chlorocarbonyl)phenyl]propyl]benzyl] aniline

To a chilled and stirred solution of title F compound (1.05 g, 3.04 mmole) in a mixture of 25 ml of dry benzene and 0.3 ml of dry dimethylformamide (hereinafter DMF) at 0° C., under nitrogen, was added dropwise oxalyl chloride (1.5 ml, 17.19 mmole). Thereafter, the solution was stirred at room temperature under nitrogen for 1.5 hours. The solvent was evaporated by a stream of nitrogen. The residue was dried in vacuo at room temperature for 1 hour to afford 1.06 g of title G compound, with consistent spectral data.

H. N-Hydroxy-N-methyl-4-[3-(N-benzyl-N-phenyl amino)-propyl]benzamide

To a stirred solution of N-methylhydroxylamine hydrochloride (600 mg, 7.18 mmole) in a mixture of 15 ml of THF and 5 ml of water was added triethylamine (4.5 ml, 3.23 mmole). A solution of title F compound (1.06 g, 2.91 mmole) in 20 ml of dry THF was then added dropwise. The resulting solution was stirred for 16 hours, adjusted to a pH of 5.5 (with 5% hydrochloric acid), most of the THF removed in vacuo, saturated with sodium chloride and extracted three times with ethyl ether. The combined extracts were washed with dilute brine, dried and evaporated to give a gum. The gum was chromatographed to give 920 mg of title H compound, with consistent spectral data, as an oil.

I. N-Hydroxy-N-methyl-4-[3-(phenylamino)propyl]benzamide

A mixture of title H compound (920 mg, 2.46 mmole) and 5% palladium on carbon (100 mg) in 75 ml of methanol was hydrogenated at room temperature under atmospheric pressure for 2 hours. The resulting mixture was filtered, washing with methanol. The filtrate was concentrated in vacuo and chromatographed to afford 250 mg of title I compound, with consistent spectral data, m.p. 93°–94° C.

EXAMPLE 2

N-Hydroxy-4-[3[(4-hydroxyphenyl)amino]propyl]-N-methylbenzamide

A. 4-(3-Bromopropyl)-benzoic acid

A complex of triphenyl phosphine (3.16 g, 12 mmole) and N-bromosuccinimide (2.14 g, 12 mmole) was prepared by stirring these in 35 ml of benzene in an ice bath for 10 minutes and at room temperature for 1 hour. A solution of 4-(3-hydroxy propyl)-benzoic acid (1.08 g, 6.0 mmole), prepared as described in Example 1, step A, in 15 ml of dry methylene chloride was added to the complex and the stirring was continued for 30 minutes. The so-formed mixture was then concentrated, diluted with 50 ml of ethyl ether and a solution of sodium carbonate (1.27 g, 12 mmole) in 50 ml of water and stirred vigorously. The ethyl ether layer was separated and the aqueous layer was extracted again with ethyl ether. The aqueous layer was acidified (with 10% hydrochloric acid) and extracted twice with ethyl ether. These extracts were combined, washed, dried, evaporated and chromatographed to afford 1.2 g of title A compound, with consistent spectral data, as a colorless solid, m.p. 116°–117° C.

B. 4-(3-Bromopropyl)-benzoyl chloride

To a cooled and stirred solution of title A compound (500 mg, 2.05 mmole) in 15 ml of dry benzene was added oxalyl chloride (0.6 ml) followed dropwise by a solution of dry DMF (0.2 ml) in dry benzene (2.0 ml). Following a vigorous gas evolution, the mixture was stirred at room temperature for 1 hour, evaporated and dried to afford 570 mg of title B compound, with consistent spectral data, as a gummy solid.

C. O-Benzyl-N-methyl hydroxylamine

To a stirred solution of O-benzylhydroxyl amine hydrochloride (1.59 g, 10 mmole) in 15 ml of dry HMPA containing dry sodium bicarbonate (3.36 g, 40 mmole) was added methyl iodide (1.5 g, 11 mmole). After 5 hours the resulting mixture was diluted with 30 ml of water and 20 ml of brine and extracted three times with ethyl ether. The extracts were combined, washed, dried and evaporated to produce the crude product as an oil. The oil was chromatographed to afford 800 mg of title C compound, with consistent spectral data.

D. N-Benzyloxy-N-methyl-4-(3-bromopropyl)benzamide

A solution of title C compound (548 mg, 4.0 mmole) in dry THF (10 ml) containing triethylamine (1.1 ml, 8.0 mmole) was cooled and stirred in an ice bath. A solution of title C compound (570 mg, ~2.05 mmole, crude) in dry THF (10 ml) was added. A deep purple color developed. After 1 hour, the mixture was diluted with 10% hydrochloric acid (25 ml) and brine (75 ml and extracted three times with ethyl ether. The extracts were combined, washed with brine, dried and evaporated to afford a dark pink colored oil. The oil was chromatographed on a column of silica gel to give 690 mg of title D compound, with consistent spectral data, as a light-purple-colored oil.

E. N-Benzyloxy-4-[3-[(4-hydroxyphenyl)amino]propyl]-N-methyl benzamide

A stirred solution of title D compound (690 mg, 1.97 mmole) in dry HMPA (8.0 ml) containing a suspension of dry NaHCO$_3$ (504 mg, 6.0 mmole) was mixed with p-aminophenol (654 mg, 6.0 mmole) and heated under an atmosphere of nitrogen in a bath at 75° for 1.0 hour. The mixture was then cooled to room temperature, diluted with water (50 ml) and extracted twice with ethyl ether. The extracts were combined, washed with water, dried and evaporated to afford the crude product as an oil. The oil was chromatographed on a column of silica gel to give 670 mg of title E compound, with a consistent spectral data, a slightly colored thick oil.

F. N-Hydroxy-4-[3-[(4-hydroxyphenyl)amino]propyl]-N-methylbenzamide

A solution of title E compound (630 mg, 1.67 mmole) in methanol (30 ml) containing 5% palladium on carbon (50 mg) was stirred under an atmosphere of hydrogen for 1 hour. It was then filtered through a bed of celite, washing with small amounts of methanol. The filtrate and the washings were combined and evaporated to afford a thick oil. The oil was crystallized from ethyl acetate:hexane (7:3) followed by drying to afford 320 mg of title F compound, with consistent spectral data, as a brownish-gray solid, m.p. 152°-153° C.

EXAMPLE 3

N-Hydroxy-N-methyl-4-(2-phenoxyethoxy)benzamide

A. Mixture of p-hydroxybenzoic acid and 4-(2-Phenoxy ethoxy)benzoic acid

A mixture of 50% NaH/paraffin (960 mg, 90 mmole), dry DMF (35 ml) and p-hydroxybenzoic acid (1.2 g, 10 mmole) was heated in a bath at 120° for 30 minutes resulting in a thick white solid. After dilution with more DMF (20 ml), alpha-bromophenetole (2.01 g, 20 mmole) was added and the heating continued for another 18 hours. Water (5.0 ml) and solid sodium hydroxide (500 mg) were added and the mixture was heated again for 15 minutes. Most of the DMF was then removed by distillation in vacuo. The residue was diluted with water (150 ml) and extracted twice with ether. The extracts were discarded. The aqueous layer was acidified with concentrated hydrochloric acid and extracted three times with ethyl acetate. The extracts were combined, washed with brine, dried and evaporated to afford 1.4 g of a mixture of p-hydroxybenzoic acid and 4-(2-phenoxy ethoxy)benzoic acid, with consistent spectral data, (1:3) as a solid.

B. 4-(2-Phenoxy ethoxy)benzoic acid, methyl ester

The mixture from step A (1.4 g) was dissolved in a mixture of methanol (10 ml) and chloroform (40 ml) and a slight excess of a solution of diazomethane in ether was added resulting in a very fast reaction. The solution was then evaporated to dryness. The residue was dissolved in ether (100 ml) and stirred vigorously with 1N sodium hydroxide (50 ml) for 1 hour. The ether layer was separated, washed once with water (10 ml), dried and evaporated to afford 1.0 g of title B compound, with consistent spectral data, as a solid, m.p. 92°-93° C.

C. 4-(2-Phenoxy ethoxy)benzoic acid

A solution of title B compound (1.0 g, 3.98 mmole) in THF (25 ml) containing 1N lithium hydroxide (15 ml) was refluxed under stirring in an atmosphere of nitrogen for 24 hours. The mixture was then concentrated in vacuo, diluted with water (100 ml) and acidified with concentrated hydrochloric acid. The so-treated material was isolated by filtration, washed with water, dried and evaporated to afford 900 mg of title C compound, with consistent spectral data, as a solid, m.p. 198°-199° C.

D. N-Hydroxy-N-methyl-4-(2-phenoxyethoxy)benzamide

A solution of title C compound (300 mg, 1.16 mmole) and oxalyl chloride (1.5 ml, 16.9 mmole) in dry benzene (7.5 ml) was cooled down to 0°, treated with dry DMF and stirred at 0° for 30 minutes under nitrogen and at room temperature for one hour. The excess oxalyl chloride and solvent were removed and the residual solid dried in vacuo for one hour. This acid chloride was dissolved in dry THF (2.1 ml) and added dropwise with stirring into a cold solution of 98% methylhydroxylamine hydrochloride (204.3 mg, 2.40 mmole) and triethylamine (0.6 ml, 4.88 mmole) in THF (4.5 ml) and water (4.5 ml). The mixture was stirred at 0° for 30 minutes and at room temperature for 5 hours, diluted with water (15 ml) and extracted twice with dichloromethane (80 ml). The combined organic extracts were washed with 1N hydrochloric acid (15 ml), 5% sodium bicarbonate (8 ml) and brine (12 ml), dried, filtered and evaporated

EXAMPLE 4

N-Hydroxy-N-methyl-4-[(3-phenylpropyl)amino]benzamide

A. N-[(4-Methoxy carbonyl)phenyl benzylamine

A mixture of methyl-4-aminobenzoate (4.535 g, 30 mmole), benzyl bromide (5.134 g, 30 mmole) and anhydrous sodium bicarbonate (3.78 g, 45 mmole) in 20 ml of dry HMPA as stirred at 75° under nitrogen for 6 hours. The resulting reaction mixture was poured into 200 ml of cold water and extracted twice with ethyl ether. The combined ether extracts were washed several times with water, dried over anhydrous magnesium sulfate and evaporated in vacuo to give a solid. This was chromatographed on a silica gel column to give 6.2 g of title A compound, with consistent spectral data, as a solid.

B. N-[(4-Methoxy carbonyl)phenyl]-N-[(3-phenyl)propyl]-benzylamine

A stirred solution of dry diisopropylamine (1.0 ml, 7.14 mmole) in dry THF (40 ml) was cooled to −78° under nitrogen and 1.65M n-butyllithium in hexane (4.33 ml, 7.14 mmole) was added dropwise. After 20 minutes a solution of title A compound (1.206 g, 5 mmole) in 20 ml of dry THF was added dropwise. The mixture was stirred at −78° for 30 minutes and then gradually warmed up to 0°. 1-Bromo-3-phenylpropane (2 ml) was then added immediately, followed by dry HMPA (2 ml). The mixture was then warmed up to room temperature and stirred under nitrogen for 16 hours. Water was added and the THF was substantially removed in vacuo. The residual slurry was extracted twice with ethyl ether. The combined ether extracts were washed several times with water, dried over anhydrous magnesium sulfate and evaporated in vacuo to give a gum. This was chromatographed on silica gel to give 1.03 g of title B compound, with consistent spectral data.

C. N-[(4-Carboxy)phenyl]-N-[(3-phenyl)propyl]benzylamine

A mixture of title B compound (500 mg, 1.39 mmole) and lithium hydroxide (440 mg, 18.3 mmole) in a mixture of water (5 ml) and dioxane (20 ml) was refluxed under nitrogen for two hours. The resulting reaction mixture was cooled to room temperature, adjusted to pH=5.0 with 5% hydrochloric acid, saturated with sodium chloride and extracted twice with ethyl ether. The combined ether extracts were dried over anhydrous magnesium sulfate and evaporated in vacuo to give 450 mg of title C compound, with consistent spectral data.

D. N-[(4-Chlorocarbonyl)phenyl]-N-[(3-phenyl)propyl]-benzylamine

To a chilled and stirred solution of title C compound (200 mg, 0.578 mmole) in a mixture of DMF (2 drops) and benzene (3.5 ml) at 0° was added dropwise oxalyl chloride (0.3 ml, 3.44 mmole). After the addition was complete, the solution was gradually warmed to room temperature and stirred under nitrogen for 1 hour. The solvent was evaporated. The residue was dried in vacuo at room temperature for 1 hour to give 205 mg of title D compound, with consistent spectral data.

E. N-Hydroxy-N-methyl-4-[[(3-phenyl)propyl-N-benzyl]-amino]-benzamide

To a solution of N-methyl hydroxylamine hydrochloride (115 mg, 1.37 mmole) and triethylamine (0.85 ml, 6.10 mmole) in a mixture of THF (3 ml) and water (1 ml) was added dropwise a solution of title E compound (205 mg, 0.56 mmole) in 3 ml of dry THF. The solution was stirred at room temperature under nitrogen for a few minutes, acidified with 5% hydrochloric acid to pH=5.5, saturated with sodium chloride and extracted three times with ethyl ether. The combined ether extracts were dried over anhydrous magnesium sulfate and evaporated in vacuo to give a gum. This was chromatographed on a silica gel column to give 185 mg of title E compound, with consistent spectral data.

F. N-Hydroxy-N-methyl-4-[(3-phenylpropyl)amino]-benzamide

A mixture of title E compound (95 mg, 0.254 mmole) and 5% palladium on carbon (30 mg) in 10 ml of methanol was hydrogenated at room temperature under one atmospheric pressure for 1.5 hours. The resulting mixture was filtered through a bed of celite and washed with methanol. The filtrate and washing were combined and concentrated in vacuo to give 70 mg of N-Hydroxy-N-methyl-4-[(3-phenylpropyl)amino]-benzamide, with consistent spectral data, m.p. 107°–108°.

EXAMPLES 5 to 20

The following additional compounds within the scope of the present invention may be prepared by employing the teachings as outlined above and in the working examples.

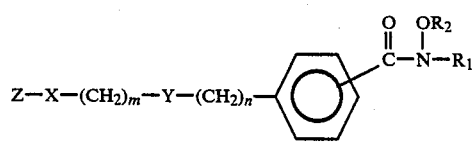

| Ex. No. | X | Y | Z | $R_1$ | $R_2$ | m | n |
|---|---|---|---|---|---|---|---|
| 5 | $-\overset{O}{\underset{\parallel}{S}}-$ | —O— | 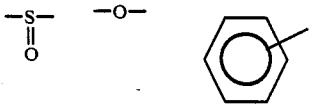 | H | —CH$_3$ | 2 | 2 |

-continued
| Ex. No. | X | Y | Z | $R_1$ | $R_2$ | m | n |
|---|---|---|---|---|---|---|---|
| 6 | —S— | —NH— | 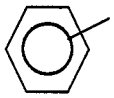 | H | —CH$_3$ | 2 | 1 |
| 7 | —S(=O)— | —S(=O)— | 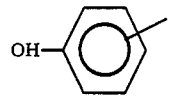 OH— | —CH$_2$CH$_3$ | H | 2 | 0 |
| 8 | —O— | —S— | 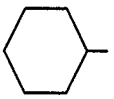 | —CH$_3$ | —CH$_3$ | 2 | 0 |
| 9 | — | —NH— | 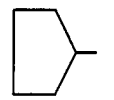 | CH$_2$—CH=CH$_2$ | —CH$_3$ | 3 | 0 |
| 10 | —NH— | — | 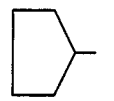 | —CH$_2$CH$_3$ |  | 3 | 2 |
| 11 | —N(CH$_3$)— | — |  | —CH$_2$CH$_3$ | C$_6$H$_5$CO— | 2 | 1 |
| 12 | —NH— | —S— | 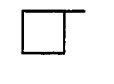 | 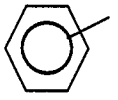 | CH$_3$CO— | 2 | 1 |
| 13 | —NH— | —NH— | 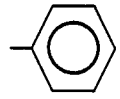 | H | —H | 2 | 3 |
| 14 | —S— | —S— | 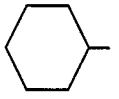 | 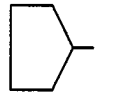 | —CH$_2$CH$_2$CH$_3$ | 1 | 3 |
| 15 | — | —NH— | 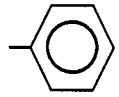—CH$_2$— | H | —CH$_3$ | 1 | 2 |
| 16 | —NH— | — | OH—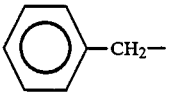 | 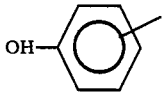 |  | 2 | 2 |
| 17 | O | — |  |  | —CH$_3$ | 2 | 1 |
| 18 | —NH— | —NH— | 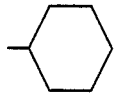 | 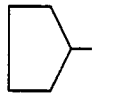 | —CH$_2$—CH=CH$_2$ | 2 | 1 |
| 19 | — | —NH— | 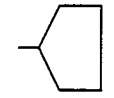 | H |  | 2 | 2 |

| Ex. No. | X | Y | Z | $R_1$ | $R_2$ | m | n |
|---|---|---|---|---|---|---|---|
| 20 | —NH— | — | 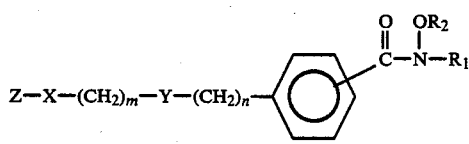 | | —$CH_3$ | 0 | 2 |

What is claimed is:

1. A compound of the formula $$Z-X-(CH_2)_m-Y-(CH_2)_n-\underset{\underset{C-N-R_1}{\overset{O}{\|}\,\overset{OR_2}{|}}}{\bigcirc}$$

wherein X and Y are each independently selected from NR, sulfur, $S(O)_g$ or a single bond, where R can be hydrogen, substituted alkyl or lower alkyl, g can be 1 or 2 and with the proviso that at least one of X and Y is other than a single bond;

Z is cycloalkyl, phenyl or naphthyl or substituted phenyl or substituted naphthyl wherein the substituents are selected from 1 or 2 halogens, 1 or 2 lower alkoxy groups, 1 or 2 hydroxyl groups, 1 or 2 alkylamine groups, 1 or 2 alkanoylamino groups, 1 or 2 amino groups, 1 or 2 nitro groups, 1 or 2 cyano groups, 1 or 2 thiol groups or 1 or 2 alkylthio groups;

$R_1$ is lower alkyl, substituted alkyl, cycloalkyl, lower alkenyl, phenyl or naphthyl or substituted phenyl or substituted naphthyl wherein the substituents are selected from 1 or 2 halogens, 1 or 2 lower alkoxy groups, 1 or 2 hydroxyl groups, 1 or 2 alkylamine groups, 1 or 2 alkanoylamino groups, 1 or 2 amino groups, 1 or 2 nitro groups, 1 or 2 cyano groups, 1 or 2 thiol groups or 1 or 2 alkylthio groups;

$R_2$ is hydrogen, lower alkyl, substituted alkyl, aroyl or acyl;

m is an integer from 1 to 4; and, n is zero or an integer from 1 to 4.

2. A compound of claim 1 wherein X is NR where R is hydrogen, Y is a single bond and Z is phenyl.

3. A compound of claim 1 wherein X is NR where R is hydrogen, Y is a single bond and Z is phenyl substituted with hydroxy.

4. A compound of claim 1 wherein X and Y are both oxygen and Z is phenylalkyl.

5. A compound of claim 1 wherein X is a single bond, Y is NR where R is hydrogen and Z is phenyl.

6. A compound of claim 1 having the name N-hydroxy-N-methyl-4-[3-(phenylamino)propyl]benzamide.

7. A compound of claim 1 having the name N-hydroxy-4-[3-[(4-hydroxyphenyl)amino]propyl]-N-methylbenzamide.

8. A compound of claim 1 having the name N-hydroxy-N-methyl-4-[(3-phenylpropyl)amino]-benzamide.

9. A composition for inhibiting allergic conditions in a mammalian species comprising an effective amount of a compound as defined in claim 1, or a pharmaceutically acceptable salt thereof, and a pharmaceutically acceptable carrier therefor.

10. A method of inhibiting $\Delta^5$-lipoxygenase which comprises administering to the circulatory system of a mammalian host an effective amount of a compound as defined in claim 1 or a pharmaceutically acceptable salt thereof.

11. The method of claim 10 wherein said compound is administered in an amount within the range of from about 1 to about 100 mg/kg.

12. A method for treating asthma in a mammalian species in need of such treatment, which comprises administering to a mammalian host an effective amount of a compound as defined in claim 1 or a pharmaceutically acceptable salt thereof.

13. A method for treating psoriasis in humans in need of such treatment which comprises administering an effective amount of the compound as defined in claim 1 or a pharmaceutically acceptable salt thereof orally, parenterally or topically.

* * * * *